US009277906B2

(12) United States Patent
White

(10) Patent No.: US 9,277,906 B2
(45) Date of Patent: Mar. 8, 2016

(54) QUICK-RELEASE HANDLE FOR RETRACTOR BLADES

(75) Inventor: William R. White, Parker, CO (US)

(73) Assignee: NSI-US, Inc., Peachtree City, GA (US)

( * ) Notice: Subject to any disclaimer, the term of this patent is extended or adjusted under 35 U.S.C. 154(b) by 984 days.

(21) Appl. No.: 13/449,555

(22) Filed: Apr. 18, 2012

(65) Prior Publication Data
US 2012/0271118 A1 Oct. 25, 2012

Related U.S. Application Data

(60) Provisional application No. 61/476,908, filed on Apr. 19, 2011.

(51) Int. Cl.
A61B 1/32 (2006.01)
A61B 17/02 (2006.01)
A61B 17/00 (2006.01)

(52) U.S. Cl.
CPC ....... A61B 17/02 (2013.01); A61B 2017/00473 (2013.01)

(58) Field of Classification Search
CPC ...... A61B 1/32; A61B 17/02; A61B 17/0206; A61B 17/0293; A61B 2017/0046; A61B 2017/00367; A61B 2017/00464
See application file for complete search history.

(56) References Cited

U.S. PATENT DOCUMENTS

| 4,934,352 | A | | 6/1990 | Sullivan, Jr. | |
|---|---|---|---|---|---|
| 5,882,298 | A | | 3/1999 | Sharratt | |
| 5,902,233 | A | * | 5/1999 | Farley et al. | 600/213 |
| 5,984,865 | A | | 11/1999 | Farley et al. | |
| 5,993,385 | A | * | 11/1999 | Johnston et al. | 600/213 |
| 6,042,540 | A | * | 3/2000 | Johnston et al. | 600/213 |
| 6,206,826 | B1 | * | 3/2001 | Mathews et al. | 600/210 |
| 6,206,828 | B1 | * | 3/2001 | Wright | 600/232 |
| 6,241,729 | B1 | | 6/2001 | Estes et al. | |
| 6,322,499 | B1 | | 11/2001 | Evans et al. | |
| 6,506,151 | B2 | | 1/2003 | Estes et al. | |
| 6,733,444 | B2 | * | 5/2004 | Phillips | 600/213 |
| 6,805,666 | B2 | | 10/2004 | Holland et al. | |
| 6,887,197 | B2 | * | 5/2005 | Phillips | 600/213 |
| 7,537,565 | B2 | * | 5/2009 | Bass | 600/219 |
| 7,569,014 | B2 | * | 8/2009 | Bass et al. | 600/213 |
| 7,588,537 | B2 | * | 9/2009 | Bass | 600/234 |
| 7,722,618 | B2 | | 5/2010 | Estes et al. | |
| 8,066,710 | B2 | | 11/2011 | Estes et al. | |
| 8,226,554 | B2 | * | 7/2012 | McBride et al. | 600/219 |
| 2002/0077530 | A1 | * | 6/2002 | Velikaris et al. | 600/213 |
| 2005/0020885 | A1 | * | 1/2005 | Rein et al. | 600/228 |
| 2006/0178566 | A1 | * | 8/2006 | Fetzer | 600/234 |

* cited by examiner

Primary Examiner — Mary Hoffman
(74) Attorney, Agent, or Firm — Dorr, Carson & Birney, PC

(57) ABSTRACT

A quick-release handle is used in positioning a retractor blade in a surgical site and securing the retractor blade to a retractor frame. The retractor blade has a generally cylindrical post for removably engaging a retractor frame, an alignment groove on its top surface, and an annular recess extending around the post. The quick-release handle has a head with a U-shaped flange for sliding engagement with the annular recess and the upper portion of the post. The handle also contains a sliding rod actuated by a thumb-slide mechanism to engage the alignment groove on the retractor blade post. In particular, a locking tongue extending from the distal end of the rod engages the alignment groove, while a protrusion extending from the rod engages the annular recess, thereby maintaining proper rotational alignment between the handle and retractor blade.

14 Claims, 5 Drawing Sheets

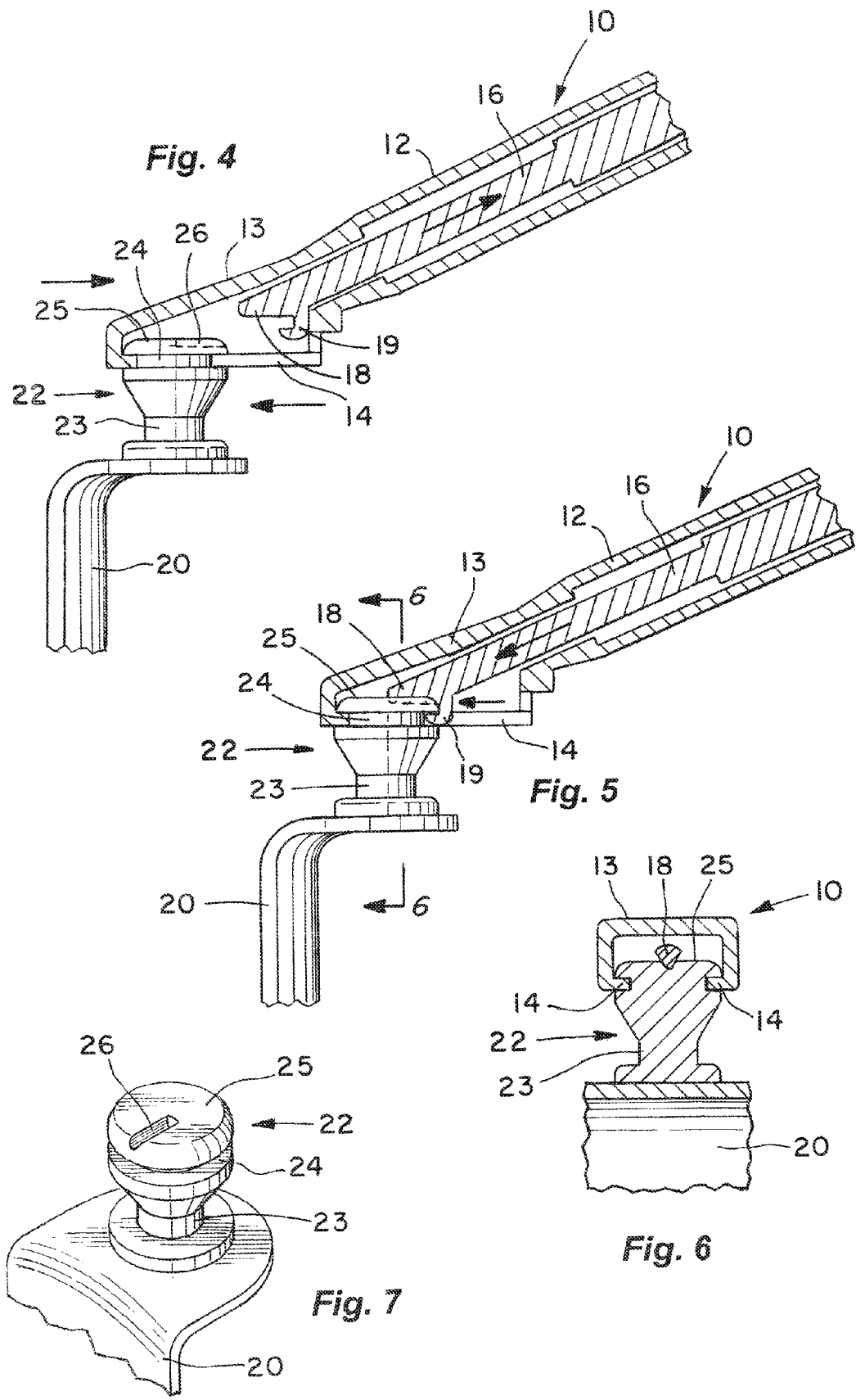

QUICK-RELEASE HANDLE FOR RETRACTOR BLADES

RELATED APPLICATION

The present application is based on and claims priority to the Applicant's U.S. Provisional Patent Application 61/476,908, entitled "Quick-Release Handle For Retractor Blades," filed on Apr. 19, 2011.

BACKGROUND OF THE INVENTION

1. Field of the Invention

The present invention relates generally to the field of surgical retractors. More specifically, the present invention discloses a quick-release handle for use in attaching a retractor blade to a retractor frame.

2. Statement of the Problem

Surgical retractors typically employ a retractor frame positioned outside and above the surgical site of the patient's anatomy to provide structural support for a number of removable retractor blades that retract the patient's tissue. One conventional type of retractor blade incorporates a round post extending upward from the top of the blade that can be removably engaged by a U-shaped latch mechanism on an adjustable arm extending from the retractor frame. A plurality of these retractor blades and adjustable arms may be required for proper retraction of tissue at a surgical site. A handle is commonly used to temporarily grip the post of a retractor blade as it is positioned within the surgical site and then secured to the latch mechanism on the retractor frame. The handle is then released and removed.

Some conventional retractor systems utilize a handle with a "twist" mechanism to engage the post of a retractor blade into the handle. The handle is then used to position the blade into the proper position within the surgical site according to patient anatomy and surgical procedure. The retractor frame is then positioned to connect to the post of the retractor blade. Once this interface is achieved, the handle is released from the post of the retractor blade and removed from the surgical site. Existing handles also utilize a twisting motion to release the handle from the post of the retractor blade after the retractor blade has been secured to a latch mechanism on the retractor frame. This twisting motion can apply a torque that rotates the blade with respect to the retractor frame and the patient, thereby causing potential misalignment of the retractor blade with regard to the surgical site. The resulting misalignment may necessitate the surgeon to start over, reattach the handle to the post of the retractor blade, and then realign the blade with respect to the retractor frame.

A second disadvantage of this type of "twist" system is the potential for misalignment of the retractor blade in relation to the handle. The resulting crooked blade alignment within the handle may require the surgeon to repositioned the blade within the handle. These misalignment issues can lead to additional operating room time, related costs, corrective alignment of the blade within the handle, and possibly tissue retraction failure, thereby creating potential negative procedural affects.

The prior art in this field also includes a number of other types of quick-release handles for retractor blades. For example, U.S. Pat. No. 6,506,151 (Estes et al.) and a number of related patents show a quick-release handle having a sliding rod with a distal tip that engages the annular recess around the post of a retractor blade (see FIG. 1(b) of Estes et al.). However, this handle is specifically designed to enable the tip of the rod to engage the retractor blade post in any of plurality of rotational orientations. In other words, the Estes handle does not lock the retractor blade in a predetermined rotational position with respect to the handle.

Solution to the Problem

The present quick-release handle addresses these shortcomings in conventional retractor systems by using a unique interface between the handle and the post of the retractor blade. This design incorporates a thumb-actuated slide mechanism in the handle that provides a self-aligning interface with the post of a retractor blade via a tongue-and-groove interface. In particular, a U-shaped flange on the head of the handle slides over the upper portion of the post to engage the handle to the post of the retractor blade. The handle also incorporates a thumb-slide mechanism that actuates a locking tongue to engage an alignment groove on the top of the blade post to provide a positive lock maintaining proper rotational alignment between the handle and retractor blade. The thumb slide mechanism also actuates an opposing finger or protrusion to engage an annular recess running around the retractor blade post. This design assures that the retractor blade will be in proper rotational alignment when loaded into the handle.

The handle can then be used to position the retractor blade in the surgical site and secure the post of the retractor blade to the retractor frame. After these steps are completed, the handle is released from the retractor blade by actuating the thumb slide proximally, and sliding the handle off the blade post. This release motion eliminates any significant torque on the retractor blade and maintains the correct positioning of the blade within the surgical site. This system provides a quick and easy solution for the surgeon to properly align and attach retractor blades to the handle and the retractor frame, thereby reducing operating room time, frustration, and related costs.

SUMMARY OF THE INVENTION

This invention provides a quick-release handle for use in positioning a retractor blade in a surgical site and securing the retractor blade to a retractor frame. The retractor blade has a generally cylindrical post for removably engaging a retractor frame, an alignment groove on its top surface, and an annular recess extending around the post. The quick-release handle has a head with a U-shaped flange for sliding engagement with the annular recess and the upper portion of the post. The handle also contains a sliding rod actuated by a thumb-slide mechanism to engage the alignment recess on the retractor blade post. In particular, a locking tongue extending from the distal end of the rod engages the alignment groove, while a protrusion extending to the distal end of the rod engages the annular recess, thereby maintaining proper rotational alignment between the handle and retractor blade.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 4 is a detail cross-sectional view of the distal end of the handle initially engaging the post 22 of a retractor blade 20 with the rod 16 retracted.

FIG. 5 is a detail cross-sectional view of the distal end of the handle 10 with the rod 16 extended so that the locking tongue 18 and protrusion 19 engage the post 22 of the retractor blade 20.

FIG. 6 is another detail cross-sectional view of the distal end of the handle 10 and the post 22 of the retractor blade 20 taken orthogonal to FIG. 5.

FIG. 7 is a perspective view of the post 22 of a retractor blade 20 showing the groove 26.

DETAILED DESCRIPTION OF THE INVENTION

Figure 1:
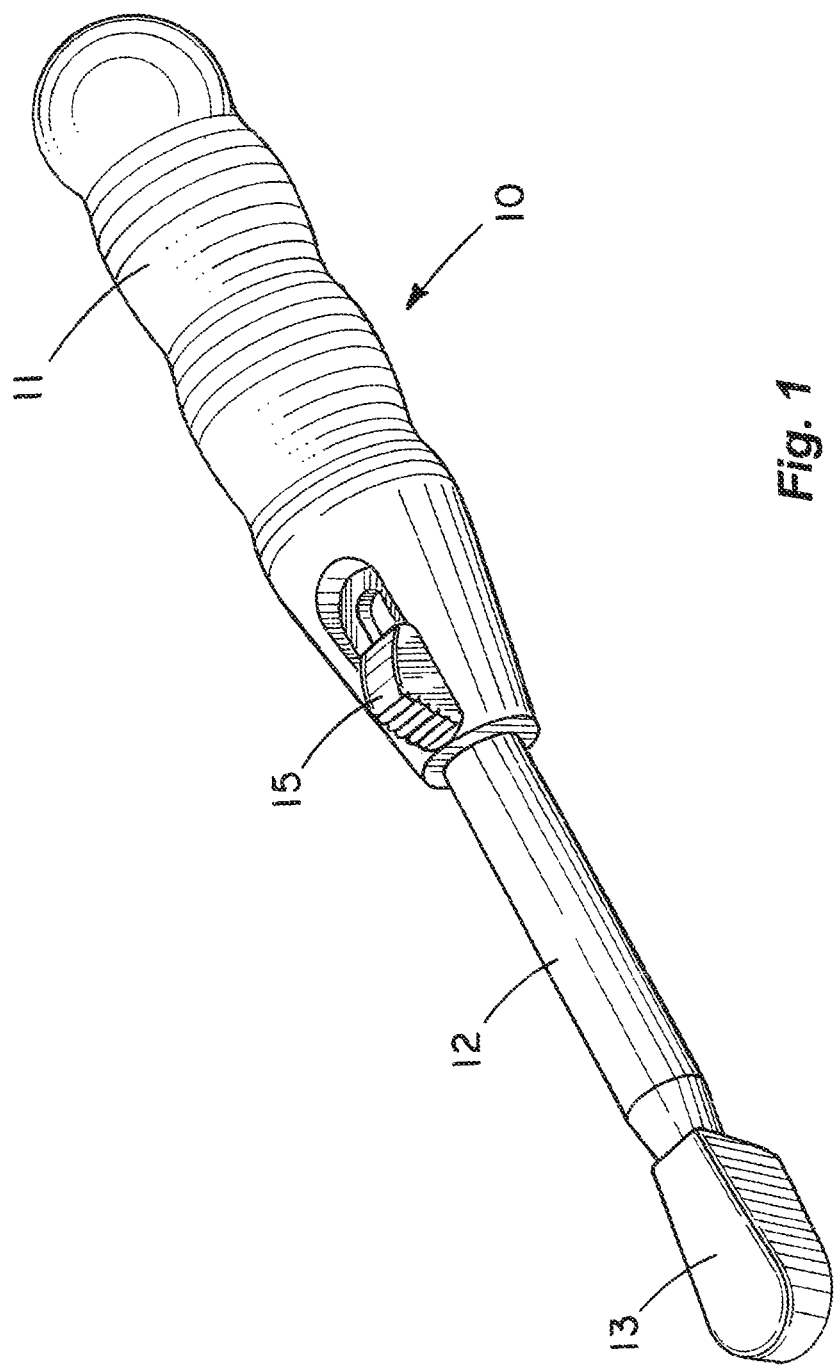
FIG. 1 is a perspective view of an embodiment of the present quick-release handle 10.
Figure 2:
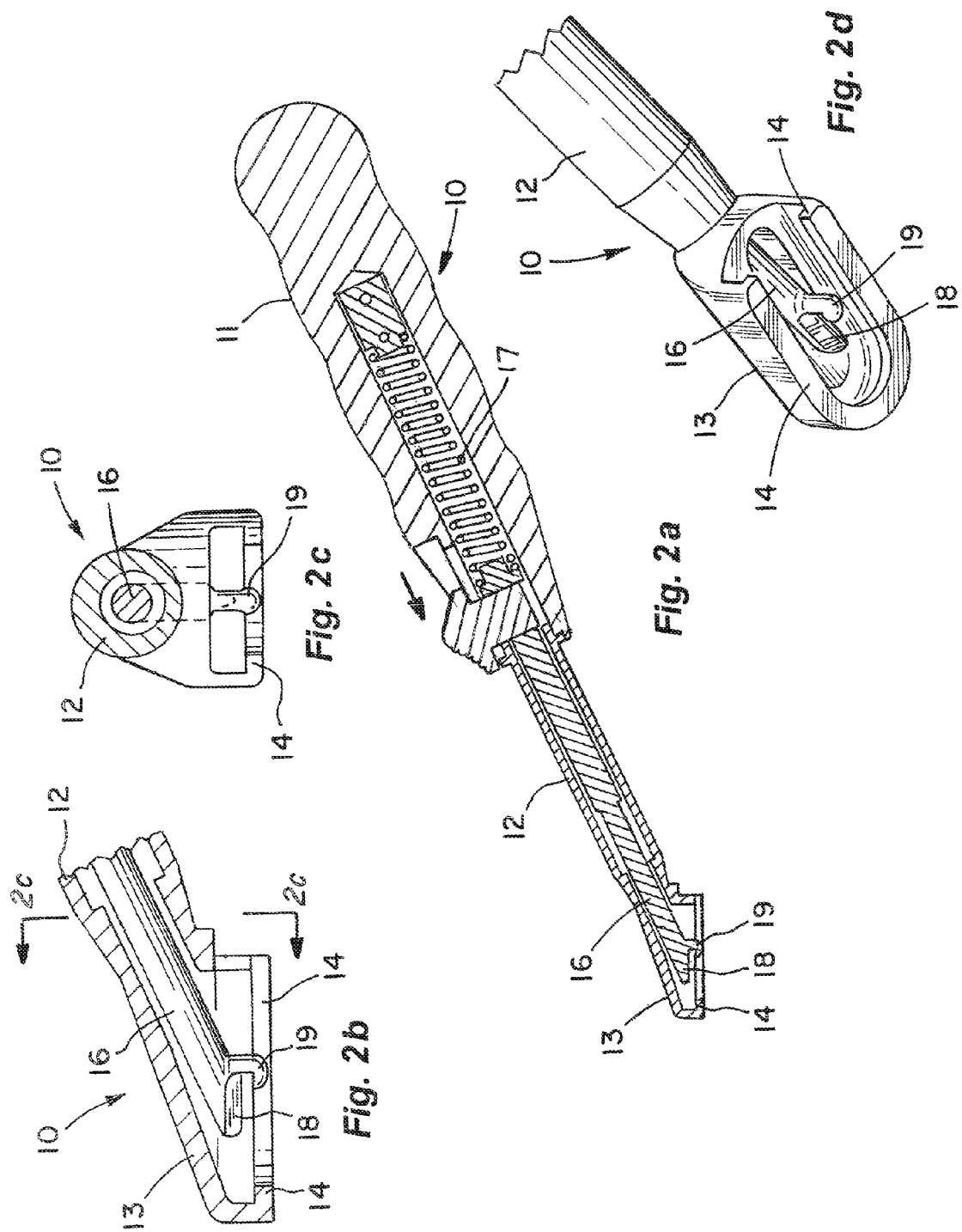
FIG. 2a is a cross-sectional view of the handle 10.
FIG. 2b is a detail cross-sectional view of the distal end of the handle 10.
FIG. 2c is another detail cross-sectional view of the distal end of the handle 10 taken orthogonal to FIG. 2b.
FIG. 2d is a detail perspective view of the distal end of the handle 10.

FIG. 1 is a perspective view of an embodiment of the present quick-release handle 10. A corresponding cross-sectional view is shown in FIG. 2a. The major components of the handle 10 include a hand grip 11 at its proximal end, with a hollow tube 12 extending toward a head 13 at its distal end for engaging the post of a retractor blade. The head 13 extends at an obtuse angle from the distal end of the tube 12.

Figure 8:
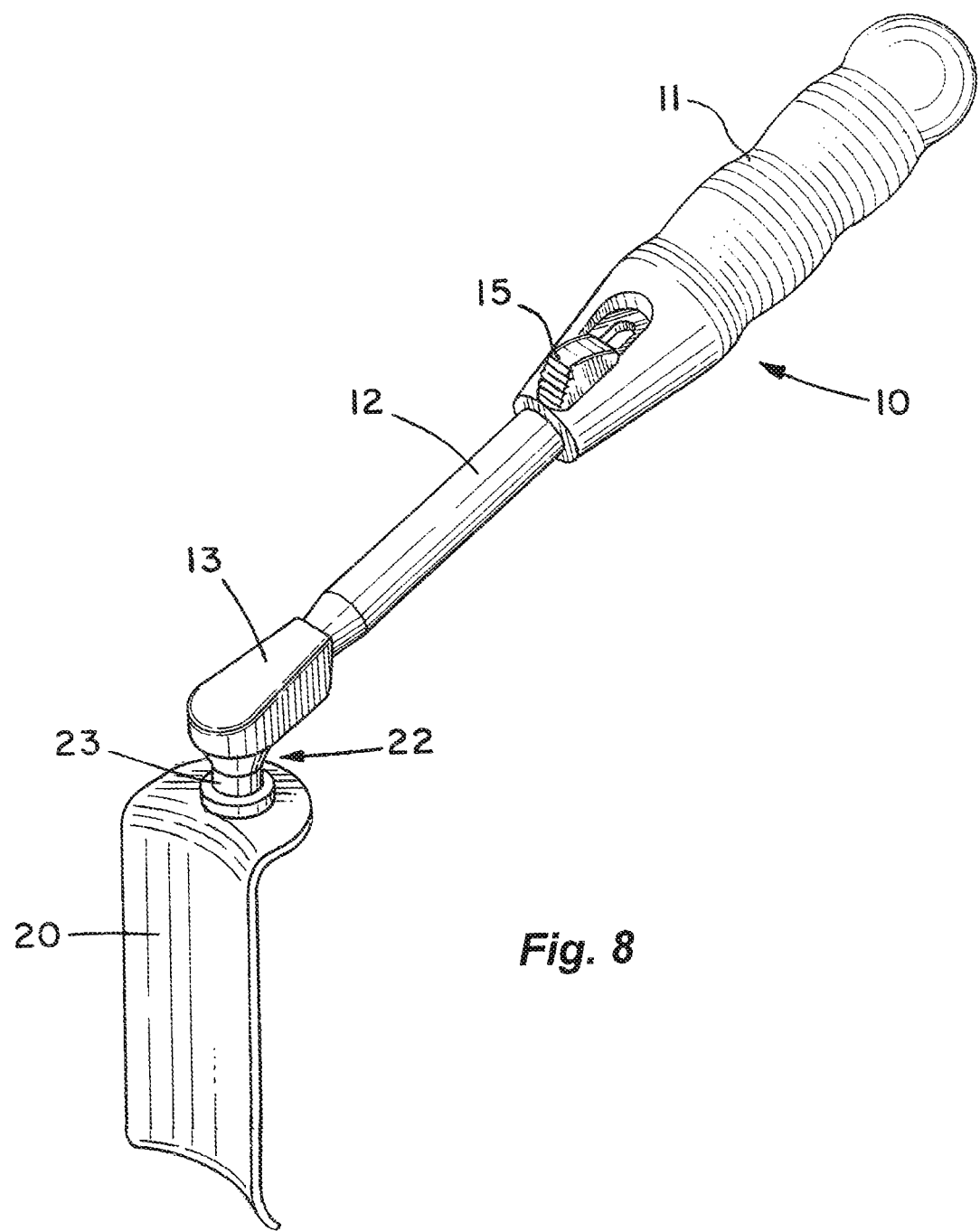
FIG. 8 is a perspective view of the handle 10 engaging the post 22 of a retractor blade 20, corresponding to FIGS. 5 and 6.

FIG. 7 is a perspective view of the post 22 of a retractor blade 20. FIG. 8 is a perspective view of the handle 10 engaging the post 22 of a retractor blade 20. As shown in FIG. 7, the post 22 is generally cylindrical, but includes a tapered neck 23 for engaging a retractor frame (not shown), and an annular recess 24 extending around the post above the neck 23. The post 22 also has a substantially flat top surface with an alignment groove 26 that extends radially across at least a portion of the top surface 25 of the post 22. In this embodiment, the alignment groove 26 has a substantially V-shaped vertical cross-section, although other cross-sectional shapes could be readily substituted.

Figure 3:
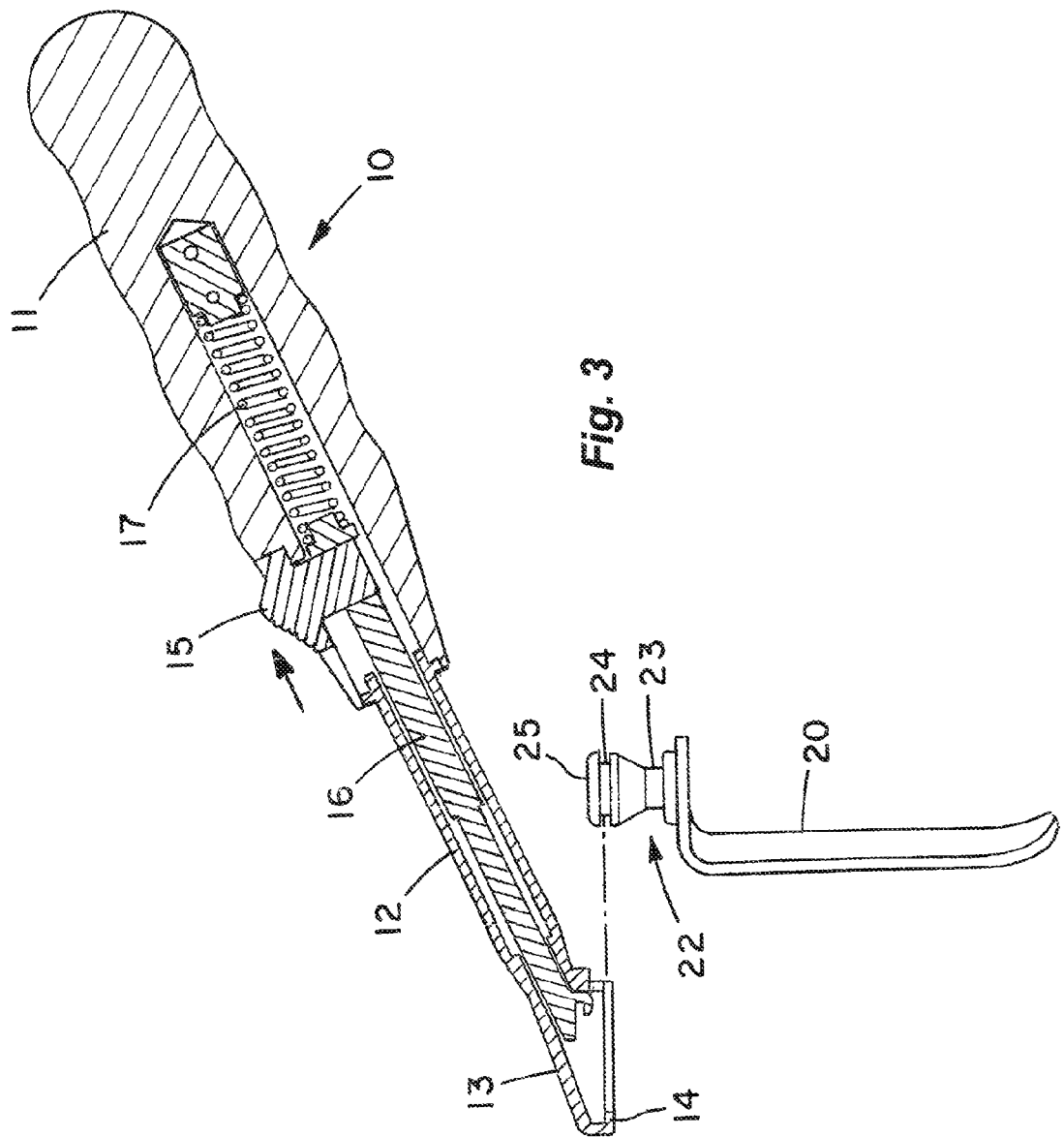
FIG. 3 is an exploded viewing showing the handle 10 in cross-section being attached to the post 22 of a retractor blade 20.

FIG. 2d is a detail perspective view of the head assembly at the distal end of the handle 10 used to engage a blade post 22. Corresponding orthogonal cross-sectional views of the head assembly are depicted in FIGS. 2b and 2c. As shown in FIG. 2d, the underside of the head 13 has a U-shaped flange 14 for receiving the annular recess 24 of the blade post 22 in sliding engagement. The U-shaped flange 14 has an open end adjacent to the distal end of the tube 12 and an opposing curved end. This essentially enables the U-shaped flange 14 of the head 13 to grip the upper portion of the blade post 22 in sliding engagement as illustrated in FIG. 3. FIG. 4 is a corresponding detail cross-sectional view of the head assembly of the handle 10 after engaging the post 22 of a retractor blade 20. Once engaged, the U-shaped flange 14 prevents vertical movement of the blade 20 with respect to the handle 10. However, at this stage the blade post 22 is not completely secured to the handle 10 because it could slide back off the flange 14.

As shown in FIGS. 2a and 3, the handle 10 also includes a slide mechanism 15, which slides a rod 16 over a short range of movement within the tube 12. The distal end of the rod 16 extends somewhat beyond the end of the tube 12 into the head 13 of the handle 10 adjacent to the open end of the U-shaped flange 14. The slide mechanism 15 can be employed to manually slide the rod between an extended position shown in FIG. 2a, and a retracted position shown in FIG. 3. For example, the slide mechanism 15 can be implemented as a thumb-actuated mechanism that is attached to the sliding rod 16 and passes through the tube 12 so that a slide tab is accessible to the user on the lower portion of the hand grip 11, as shown in FIG. 1. Optionally, the handle can also contain a spring 17 to bias the slide mechanism 15 toward the extended position shown in FIG. 2a.

A locking tongue 18 extends at an obtuse angle from the distal end of the rod 16 as shown in FIGS. 2a, 2b, 2d and 4. This locking tongue 18 has a cross-sectional shape that is complementary to that of the alignment groove 26 on the top surface 25 of the blade post 22. This enables the locking tongue 18 to engage the alignment groove 26 on the blade post 22 when the slide mechanism 15 and rod 16 are extended. The locking tongue 18 is generally located adjacent to the open end of the U-shaped flange and runs axially between, and parallel to the arms of the U-shaped flange 14 in the preferred embodiment of the present invention, as shown in FIGS. 2c and 2d. The locking tongue 18 is moved by the sliding rod 16 toward the curved end of the U-shaped flange 14 in the extended position, and retracted toward the open end of the U-shaped flange 14 in the retracted position.

In the embodiment shown in accompanying drawings, the alignment groove 26 has a substantially V-shaped cross-section. In this embodiment, the lower portion of the locking tongue has a complementary V-shape to register in the alignment groove 26 when the thumb-slide mechanism 15 and rod 16 slide to their extended position. FIG. 5 is a detail cross-sectional view of the distal end of the handle 10 with the rod 16 extended so that the locking tongue 18 engages the alignment groove 26 on the top surface 25 of the post 22 of the retractor blade 20. FIG. 6 is a corresponding orthogonal cross-sectional view.

Due to the obtuse angle between the sliding rod 16 and the head 13, the rod 16 and locking tongue 18 exert a force vector on the post 22 of the retractor blade 20 having two orthogonal force components. A normal force component (i.e., normal to the top surface 25 of the post 22) pushes downward to seat the locking tongue 18 in the alignment groove 26. A parallel component (i.e., parallel to the top surface 25 of the post 22) pushes the post 22 of the retractor blade 20 against the curved end of the U-shaped flange 14 and holds it in place.

Preferably, the upper surface 25 for the blade post 22 is generally circular, and the alignment groove 26 extends radially outward from the center point of the top surface 25 of the blade post 22, as illustrated in FIG. 7. This configuration ensures that the retractor blade 20 can only be secured to the quick-release handle 10 in one rotational orientation.

A protrusion or finger 19 also extends downward and forward from the distal end of the rod 16. In other words, the protrusion 19 extends below the locking tongue 18, as shown in FIG. 2b. In the extended position, this protrusion 19 engages the annular recess 24 on the blade post 22 to prevent the blade post 22 from sliding along the U-shaped flange 14. Thus, when the thumb-slide mechanism 15 and rod 16 are in the extended position, the blade post 22 is securely held by the handle 10. The protrusion 19 prevents the blade post 22 from sliding along the U-shaped flange, and the locking tongue 18 prevents rotation of the blade post 22. This device provides a positive, self-locking interface between the retractor blade and the handle. It also provides the surgeon with a tool that can be used as a Cloward-type retractor, as well as its primary function, which is to position the blade within the surgical site and then lock easily within the retractor frame.

When the slide mechanism 15 is retracted by the user, the rod 19, locking tongue 18 and protrusion 19 slide upward and laterally away from the blade post 22 within the head 13 of the handle 10 due to the angle of the handle tube 12, as shown in FIG. 4. This upward sliding motion lifts the protrusion 19 out of the path of the blade post 22 as it slides along the U-shaped flange 14, as illustrated in FIG. 3. For this reason, the slide mechanism is moved to its retracted position while a retractor blade 20 is either being attached to or being removed from the handle 10.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

I claim:

1. A quick-release handle for removably engaging a retractor blade having a post with an annular recess and a top surface with an alignment groove, said quick-release handle comprising:
    a hollow tube with a distal end;
    a head at the distal end of the tube having a U-shaped flange for sliding engagement with the annular recess of the post of a retractor blade;
    a rod sliding within the tube;
    a slide mechanism attached to the rod enabling manual movement of the rod between a retracted position and an extended position relative to the tube;
    a locking tongue extending from the rod for seating in the alignment groove in the top surface of the post of a retractor blade to retain the post of a retractor blade in the U-shaped flange in the extended position in a desired orientation, and retracting from the alignment groove to release the post of a retractor blade in the retracted position; and
    a protrusion extending from the distal end of the sliding rod to engage the annular recess in the post of a retractor blade and retain the post in the U-shaped flange of the head in the extended position.

2. The quick-release handle of claim 1 further comprising a hand grip on the tube, and wherein the slide mechanism further comprises a thumb-actuated slide mechanism on the lower portion of the hand grip actuating the sliding rod.

3. The quick-release handle of claim 1 wherein the slide mechanism comprises a thumb-actuated slide mechanism extending through the tube.

4. The quick-release handle of claim 1 wherein the post of a retractor blade has a substantially circular top surface with a center point, and the alignment groove extends radially outward from the center point; and wherein the locking tongue extends axially between the arms of the U-shaped flange.

5. The quick-release handle of claim 1 wherein the locking tongue extends at an obtuse angle from the sliding rod with the locking tongue substantially parallel to the U-shaped flange.

6. The quick-release handle of claim 5 wherein the sliding rod and locking tongue exert a force vector on the post of a retractor blade having a normal component seating the locking tongue in the alignment groove, and a parallel component holding the post of a retractor blade in the U-shaped flange.

7. The quick-release handle of claim 1 wherein the U-shaped flange has an open end for receiving the post of a retractor blade and an opposing curved end; and wherein the locking tongue is located adjacent to the open end of the U-shaped flange and moves toward the curved end of the U-shaped flange in the extended position.

8. The quick-release handle of claim 1 wherein the locking tongue and alignment groove have complementary V-shaped cross-sections.

9. A quick-release handle for removably engaging a retractor blade having a post with an annular recess and a top surface having an alignment groove, said quick-release handle comprising:
    a hollow tube with a distal end;
    a head extending at an obtuse angle from the distal end of the tube, said head having a U-shaped flange for sliding engagement with the annular recess of the post of a retractor blade, said U-shaped flange having an open end adjacent to the distal end of the tube and an opposing curved end;
    a rod sliding within the tube, said rod having a distal end adjacent to the open end of the U-shaped flange of the head;
    a slide mechanism attached to the rod enabling manual movement of the rod between a retracted position and an extended position relative to the tube; and
    a locking tongue extending at an obtuse angle from the distal end of the rod for seating in the alignment groove of the top surface of the post of a retractor blade to retain the post of a retractor blade in the U-shaped flange in the extended position, and retracting from the alignment groove to release the post of a retractor blade in the retracted position; wherein the rod and locking tongue exert a force vector on the post of a retractor blade in the extended position having a normal component seating the locking tongue in the alignment groove, and a parallel component holding the post of a retractor blade against the curved end of the U-shaped flange.

10. The quick-release handle of claim 9 further comprising a protrusion extending from the distal end of the sliding rod to engage the annular recess in the post of a retractor blade and retain the post in the U-shaped flange of the head in the extended position.

11. The quick-release handle of claim 10 wherein the protrusion comprises a finger extending from the distal end of the sliding rod beneath the locking tongue.

12. The quick-release handle of claim 9 further comprising a hand grip on the tube, and wherein the slide mechanism further comprises a thumb-actuated slide mechanism on the lower portion of the hand grip actuating the sliding rod.

13. The quick-release handle of claim 9 wherein the top surface of the post is substantially circular with a center point, and the alignment groove extends radially outward from the center point.

14. The quick-release handle of claim 9 wherein the locking tongue and alignment groove have complementary V-shaped cross-sections.

* * * * *